(12) United States Patent
Giori et al.

(10) Patent No.: US 12,337,022 B2
(45) Date of Patent: Jun. 24, 2025

(54) USE OF A VEGETABLE EXTRACT FROM SALVIA HAENKEI AS AN ACTIVE AGENT IN THE TREATMENT OF HEART DISEASES

(71) Applicant: Altergon S.A., Lugano (CH)

(72) Inventors: Andrea Maria Giori, Lugano (CH); Andrea Alimonti, Lugano (CH)

(73) Assignee: IBSA INSTITUT BIOCHIMIQUE SA, Lugano (CH)

( * ) Notice: Subject to any disclaimer, the term of this patent is extended or adjusted under 35 U.S.C. 154(b) by 0 days.

(21) Appl. No.: 18/576,171

(22) PCT Filed: Jul. 1, 2022

(86) PCT No.: PCT/EP2022/068287
§ 371 (c)(1),
(2) Date: Jan. 3, 2024

(87) PCT Pub. No.: WO2023/280714
PCT Pub. Date: Jan. 12, 2023

(65) Prior Publication Data
US 2024/0261357 A1    Aug. 8, 2024

(30) Foreign Application Priority Data
Jul. 5, 2021 (IT) .......................... 102021000017666

(51) Int. Cl.
*A61K 36/537* (2006.01)
*A61P 9/00* (2006.01)
*A61P 9/04* (2006.01)
*A61P 9/06* (2006.01)

(52) U.S. Cl.
CPC .............. *A61K 36/537* (2013.01); *A61P 9/00* (2018.01); *A61P 9/04* (2018.01); *A61P 9/06* (2018.01)

(58) Field of Classification Search
CPC . A61K 36/537; A61P 9/00; A61P 9/04; A61P 9/06
See application file for complete search history.

(56) References Cited

FOREIGN PATENT DOCUMENTS

| EP | 2762131 A1 * | 8/2014 | ........... A61K 36/537 |
| WO | WO-2019121427 A1 * | 6/2019 | ........... A61K 36/537 |

OTHER PUBLICATIONS

Matic I et al., "Identification of <i>Salvia haenkei as gerosuppressant agent by using an integrated senescence-screening assay", Aging, vol. 8, No. 12, Dec. 28, 2016, pp. 3223-3240 .</i>.
Search Report and Written Opinion of PCT/EP2022/068287 issued Sep. 28, 2022.
Topcu G, "Bioactive triterpenoids from salvia species", Journal of Natural Products, vol. 69, No. 3, Mar. 9, 2006, pp. 482-487.

* cited by examiner

*Primary Examiner* — Jessica Worsham
(74) *Attorney, Agent, or Firm* — Silvia Salvadori, P.C.; Silvia Salvadori

(57) ABSTRACT

The present invention relates to the use of *Salvia haenkei* extract as an active agent in the treatment of heart diseases, being able to offer a significant contribution in slowing, relieving, reducing and/or preventing alterations and damages of the cardiac tissue. Furthermore, the present invention also relates to a pharmaceutical composition comprising *Salvia haenkei* extract and suitable pharmaceutically acceptable excipients, for use in the treatment of heart diseases.

11 Claims, 5 Drawing Sheets

A

B

C

A

B

C

A

B

C

A

B

USE OF A VEGETABLE EXTRACT FROM SALVIA HAENKEI AS AN ACTIVE AGENT IN THE TREATMENT OF HEART DISEASES This application is a U.S. national stage of PCT/EP2022/068287 filed 1 Jul. 2022, which claims priority to and the benefit of Italian Application No. 102021000017666 filed 5 Jul. 2021, the contents of which are incorporated herein by reference in their entireties.

FIELD OF THE INVENTION

The present invention relates to the use of *Salvia haenkei* extract as an active agent in the treatment of heart diseases. *Salvia haenkei* extract offers a significant contribution in slowing, relieving, reducing and/or preventing alterations and damages of the cardiac tissue, both muscular and connective. Furthermore, the present invention also relates to a pharmaceutical composition comprising *Salvia haenkei* extract and suitable pharmaceutically acceptable excipients, for use in the treatment of heart diseases.

BACKGROUND

The term "heart diseases", or indifferently "cardiac pathologies", refers to a variety of acute and/or chronic pathologies, that can affect one or more of the heart components. Heart diseases represent the most frequent chronic diseases, with consequent involvement of sanitary costs. In addition, heart diseases are now the leading cause of death.

The most relevant cardiac pathologies include cardiac fibrosis, arrhythmias, long QT syndrome (QTL), heart failure or decompensation, and cardiotoxicity. Said heart diseases can be caused by various factors including high blood pressure, diabetes mellitus, myocardial infarction, chemotherapy, or heart transplant.

In cardiac fibrosis, the myocardium, the cardiac tissue composed of myocardiocytes incorporated in an extracellular matrix (ECM) of collagen fibers, remodels with increased deposit of type I collagen. Cardiac fibrosis can be: reactive to arterial hypertension and protracted overload of work, usually without loss of cardiomyocytes, infiltrative as in metabolic disorders such as sphingolipidosis, and reparative after myocardial infarction that is linked to damage to cardiomyocytes.

Cardiac fibroblasts, that are activated in an unbalanced way, differentiate into myofibroblasts, expressing growth factors, proinflammatory and profibrotic factors, and secreting high quantities of metalloproteinases and other enzymes that degrade the extracellular matrix facilitating their own migration; in addition, the deposit of collagen and other proteins leads to the formation of scars which over time make the interstitium more rigid (stiffness), compromising heart function.

Evaluation of cardiac fibrosis can be carried out by endomyocardial biopsy and magnetic resonance imaging or by measuring biomarkers of fibrosis such as serum fibronectin, TGF-β and MMPs (matrix metalloproteinase).

Long QT, or long QT syndrome, is a rare heart condition, where the recovery time of the heart's ventricles after one contraction, in preparation for the next one, is lengthened. This malfunction is detectable as an alteration in specific portions of the electrocardiographic trace (QT interval and T wave). Long QT syndrome in many cases is associated with arrhythmias, that are life-threatening changes in the myocardial rhythm. Long QT syndrome can be congenital or secondary to the intake of drugs or to alterations in blood electrolytes.

Cardiotoxicity is defined as toxicity affecting the heart during a pharmacological treatment, generally an oncological one. The best-known heart damage is left ventricular dysfunction which can lead to chronic and progressive heart failure and sometimes even death. In addition to the complete clinical evaluation with ECG, the two most used diagnostic methods are echocardiography and dosage of the two cardiac biomarkers, Troponin and Natriuretic Peptides. Traditionally, subclinical cardiac toxicity has been detected by evaluating the reduction of left ventricular ejection fraction (LVEF) with the use of echocardiography or other imaging.

In general, cardiac pathologies therefore manifest themselves as alterations in the electrophysiological function of the heart, often associated with arrhythmias and/or heart failure. Any pathology that damages the heart or decreases heart's function, altering its ability to pump oxygenated blood in all vessels and organs, has serious consequences that can manifest systemically.

Currently available therapeutic strategies for heart diseases are generally directed at slowing the heart rate, for example with beta-blocker drugs, making arrhythmias less likely to occur. To reduce the cardiac fibrosis, instead, therapies of uncertain efficacy are used, such as angiotensin converting enzyme inhibitors and angiotensin receptor antagonists, β blockers, endothelin antagonists and finally statins. The automatic implantable defibrillator in patients is instead the most used non-drug therapy for patients at high risk of sudden cardiac death. This therapy is clearly invasive.

The aim of the present invention is therefore to provide a new effective and non-invasive remedy for the treatment of cardiac pathologies, capable of acting at the level of both muscular and connective cardiac tissue.

SUMMARY OF THE INVENTION

Said object has been achieved by the use of *Salvia haenkei* extract as an active agent in the treatment of heart diseases, as reported in claim 1.

In another aspect, the present invention relates to a pharmaceutical composition comprising *Salvia haenkei* extract and suitable pharmaceutically acceptable excipients, for use in the treatment of heart diseases.

For the purposes of the present invention, said heart diseases comprise: cardiac fibrosis, arrythmia, long QT syndrome (QTL), heart failure, heart attack, and cardiotoxicity.

BRIEF DESCRIPTION OF THE FIGURES

The characteristics and the advantages of the present invention will become clear from the following detailed description, the working examples provided for illustrative purposes and the accompanying figures, wherein.

DETAILED DESCRIPTION OF THE INVENTION

Figure 1:
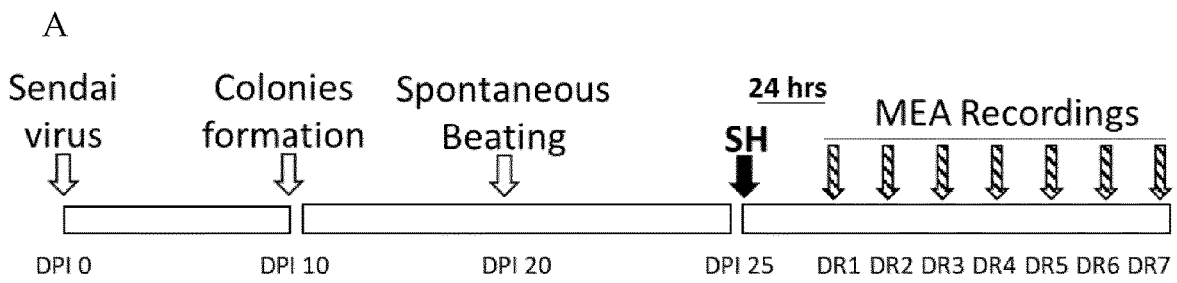
FIG. 1 shows: (A) a scheme of the protocol of the in vitro experiment of Example 2 (SH=*Salvia haenkei* extract; MEA=multielectrodes array), (B) an exemplary ECG trace (QT interval is shown) and (C) the results of the QT recordings of SH treated and non-treated beating cardiomyocytes (CMs) from unaffected human subjects.
Figure 1:
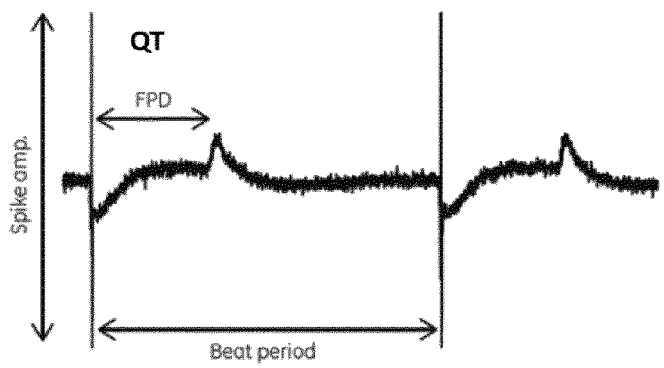
Figure 1:
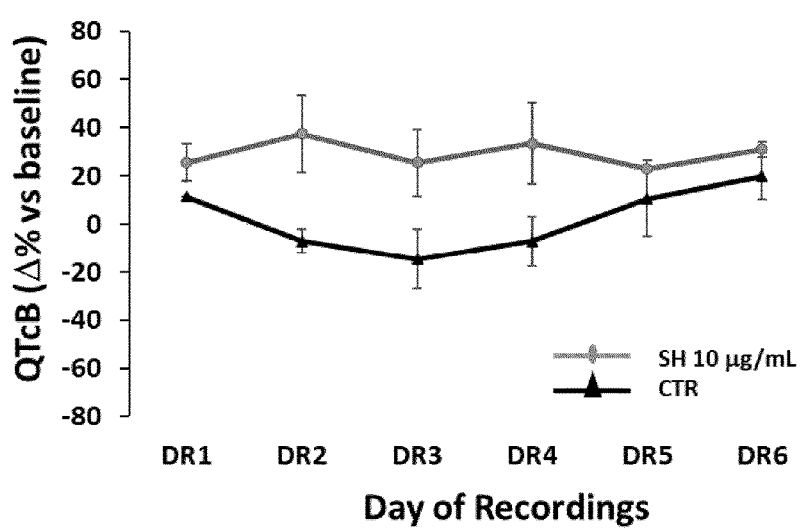

*Salvia haenkei* is a shrub coming from Bolivia and Peru, commonly called "prawn sage" due to the colour and shape of its shrimp-like flowers. Morphologically, *Salvia haenkei* is characterized by lance-shaped leaves with dentate margins whose length exceeds 12 cm. Their colour is light green and the surface is wrinkled. The inflorescence is very long, over 20 cm and is defined as "raceme", i.e., the flowers are inserted at the level of the central axis through the peduncles of the same length at different heights along the same flower axis.

For the preparation of the extract, the aerial parts of the plant are generally used, i.e., stem, leaves, flowers or mixtures thereof. These parts can be used fresh or after drying under controlled conditions. In both cases, the individual parts or mixtures thereof are contacted with a suitable extraction solvent, by using conventional extraction methods, such as maceration or percolation, or more complex techniques, such as for example extraction with ultrasound, microwaves, pressure or supercritical fluids.

After separation of the exhausted plant, the extract can be used as such, or after substitution of the extractive solvent with one more solvent suitable for human use (such as glycerine or glycol, if not used in the extraction phase). Preferably, the extracting solvent is removed to give a dry extract. For the removal of the extractive solvent, the preferred techniques are evaporation at reduced pressure and low temperature, and atomization.

The extract can also be subjected to subsequent purification steps, to remove potential contaminants (such as lipophilic pesticides), impurities (such as chlorophyll) or to increase the concentration of secondary metabolites.

The so obtained *Salvia haenkei* extract contains a pool of terpenoid compounds, in particular diterpenoids and triterpenoids (Almanza, G. et al., (1997) Clerodane diterpenoids and an ursane triterpenoid from *Salvia haenkei*, Computer-assisted structural elucidation, Tetrahedron, 53 (43), pp. 14719-14728), as well as gallic acid and its derivatives, and chlorogenic acid and its derivatives. Some of these compounds are specific to this species of *Salvia* and differentiate it from other species of the same genus, contributing reasonably to the characteristic activity of its extracts.

The dry extract can be added with suitable excipients, for example to make it smoother, less hygroscopic or standardized in the content of secondary metabolites. Among the excipients that can be used are, for example, silica, maltodextrins, microcrystalline cellulose.

Among the solvents suitable for the preparation of *Salvia haenkei* extract, those with a medium polarity are preferably selected, as being capable of effectively extracting the secondary metabolites of the plant. Preferably, such extraction solvents have a dielectric constant of 8 to 60.

Examples of usable extraction solvents are alcohols having up to 4 carbon atoms, including diols and triols, aldehydes, ketones, organic esters, chlorinated compounds, and mixtures thereof. When miscible, such solvents can also be used in mixture with water.

Preferred solvents include methanol, ethanol, isopropanol, butanol, ethylene glycol, propylene glycol, glycerol, acetone, ethyl acetate and mixtures thereof, as such or mixed with water.

In preferred embodiments, said extraction solvent is a water-alcohol solution, even more preferably it is a 40-80% alcohol solution. Said alcohol is preferably methanol or ethanol. Embodiments in which the extraction solvent is a 60-80% ethanol solution are particularly preferred.

Preferably, the preparation of said *Salvia haenkei* extract comprises the steps of:
1. collecting aerial parts of *Salvia haenkei*,
2. extracting with a solvent,
3. separating the plant exhausted from the liquid extract, and
4. removing the solvent to give the dry extract.

The aerial parts of step 1. may be fresh or preliminarily dried. If the aerial parts are fresh, just harvested, the greater amount of water physiologically present in the plant shall be taken into account.

The invention therefore relates to the use of *Salvia haenkei* extract as active agent for use in the treatment of heart diseases.

For the purposes of the present invention, the term "treatment", is meant to include administration of *Salvia haenkei* extract, or of a pharmaceutical composition comprising said extract, to a subject with, or at risk of developing, heart disease for the purpose of improving the overall condition of the subject's heart tissue, as well as for the purpose of slowing, relieving, reducing, and/or preventing any alteration of the functioning of the heart tissue in the subject.

Preferably, said heart diseases are: cardiac fibrosis, arrhythmia, long QT syndrome (QTL), heart failure, heart attack, or cardiotoxicity.

These heart diseases can be caused by various factors including high blood pressure, diabetes mellitus, myocardial infarction, chemotherapy, hypercholesterolemia or heart transplant. Optionally, said cardiac pathologies are induced by drugs, such as for example chemotherapy drugs.

Preferably, said extract is to be administered to a subject in need thereof in a dose of 0.1-1500 mg per day.

In preferred embodiments, said extract is to be administered via systemic route, more preferably by oral administration, in a dose of 1-5000 mg per day, the effective dosage being a function of the extent and severity of the disease to be treated.

Preferably, the daily dose of medicaments is about 1500 mg, preferably from 0.1 to 1000 mg, preferably administered in divided manner about once or 2-3 times a day.

In another aspect, the present invention relates to a pharmaceutical composition comprising *Salvia haenkei* extract and pharmaceutically acceptable carriers, for use in the treatment of heart diseases.

In another aspect, the present invention relates to a food supplement comprising *Salvia haenkei* extract, for use in the treatment of heart diseases.

Said pharmaceutical composition or food supplement can be administered via oral route. Preferably, the pharmaceutical composition or food supplement comprising *Salvia haenkei* extract is in liquid form, more preferably *Salvia haenkei* extract is in a concentration of 0.1-500 mg/ml of the composition or supplement, more preferably 1-100 mg/ml.

Preferably, the pharmaceutical composition or food supplement comprising *Salvia haenkei* extract is in solid form, more preferably *Salvia haenkei* extract is in a concentration of 0.1-500 mg/mg of the composition or supplement, more preferably 1-100 mg/mg.

Preferably, the pharmaceutical composition comprises *Salvia haenkei* extract and at least one further active agent, selected from the group consisting of: a cardiotonic agent, an antiarrhythmic agent, a vasodilator, an antihypertensive agent, an antiplatelet agent and a diuretic.

The preparations for oral administration of the pharmaceutical composition comprising the *Salvia haenkei* extract may be in the form of tablets, capsules, lozenges, orodispersible films, soft gelatin capsules, granulates or powder, orodispersible powder, liquid solutions, dressing, or suspensions. As known in the art, tablets, capsules and lozenges may contain usual excipients in addition to the active ingredient, for example extenders such as lactose, calcium phosphate, sorbitol and the like; lubricants such as magnesium stearate, polyethylene glycol (PEG), binding agents such as polyvinyl pyrrolidone, gelatine, sorbitol, acacia, flavoring agents, disintegrating agents and dispersing agents.

Liquid preparations, generally in the form of aqueous or oily solutions or suspensions, may contain conventional additives such as dispersing agents.

All the pharmaceutical formulations described above can be prepared by methods known in the pharmaceutical technique.

It should be understood that all the aspects identified as preferred and advantageous for the *Salvia haenkei* extract are to be deemed as similarly preferred and advantageous also for the pharmaceutical compositions and uses thereof.

It should be also understood that all the combinations of preferred aspects of the *Salvia haenkei* extract of the invention, as well as of the pharmaceutical compositions and uses of the same, as above reported, are to be deemed as hereby disclosed.

Below are working examples of the present invention provided for non-limiting, illustrative purposes, demonstrating the efficacy of *Salvia haenkei* extracts in the treatment of heart diseases.

EXAMPLES

Example 1

Preparation of *Salvia haenkei* Extracts 10 kg of aerial parts of *Salvia haenkei* are harvested from field crops, which are then subjected to a drying process in a ventilated dryer under controlled conditions.

In this way, 1.95 kg of dried plant are obtained, which are minced into a bladed mill to give dried and ground *Salvia haenkei*.

This is used as raw material for the subsequent solvent extractions carried out as described below:
1. 100 g of dried and ground *Salvia haenkei* are introduced into a static percolator and covered completely with 200 ml of a water and ethanol 30-70% v/v mixture. It is left to stand for 2 hours and the extraction solvent (170 ml) is recovered from the bottom of the percolator, which is set aside (extract 1);
2. the humid plant left in the percolator is covered with a new 70% aqueous ethanol (170 ml) aliquot, leaving it to rest for 2 hours. The solvent is recovered (165 ml—extract 2);
3. the extraction described in point 2 is repeated until the dry residue of the extract recovered is less than 5% of the total dry residue extracted up to that moment. At that point, the extraction is considered completed and the spent moist plant is eliminated. 6 extractions are required;
4. the extracts obtained from the individual extraction steps (from extract 1 to extract 6) are combined, filtered and concentrated in a rotary evaporator under vacuum, at a low temperature. It is proceeded until a concentrated, viscous solution (35 ml) is obtained;
5. the concentrated extract is transferred to a steel tray and inserted into a under vacuum cabinet dryer, with heating set at 30° C. After 12 hours, the solvent is completely removed (extract weight loss less than 10%, i.e., dry residue higher than 90%). 14.3 g of integral dry extract are obtained. The ratio drug:extract (DER) is 7:1 (extract 1A).
6. the dried extract obtained is added with 10 g of maltodextrin (DE 10) to improve its consistency and the mixture is milled and sieved, thus obtaining 23.7 g of ground dry extract.

By applying the same procedure but different extracting solvents different native dry extracts were prepared.

The table summarizes the results of the various extractions:

| extract | extraction solvent | DER |
|---------|-------------------|-----|
| 1A | ethanol:water 70:30 | 7:1 |
| 1B | ethanol:water 95:5 | 9.5:1 |
| 1C | acetone | 11:1 |
| 1D | methanol | 8:1 |
| 1E | ethyl acetate | 15:1 |
| 1F | water | 5:1 |
| 1G | methanol:water 50:50 | 6:1 |

In the following Examples, a hydroalcoholic extract of *Salvia haenkei* of Example 1A was used, briefly referred to as "SH".

For in vitro experiments the extract was reconstituted with pure ethanol to reach a stock concentration of 10 mg/ml (SH is not water soluble at this concentration) and kept at −20° C. Working solutions were obtained by diluting the stock solution in water-based RPMI culture medium at concentration of 10 µg/ml, 100 g/ml and 300 µg/ml depending on the assay.

For in vivo experiments, considering that a water intake for adult rat is about 30-40 ml/day, 1.25 gr of SH extract was diluted in 300 ml of water, achieving a daily dose of about 0.5 mg/Kg (extract/body weight).

Example 2

SH Effects on Electrophysiological Properties of Beating Human iPS-CM (Basal)

In vitro tests were performed on human specialized cardiac cells, cardiomyocytes (CMs), derived from iPSC. Human iPSCs were generated by overexpressing the four Yamanaka's factors (Oct3/4, Sox2, Klf4, c-Myc) in adult somatic cells. Stable colonies of stem cells were than ri-differentiated into CM, as described by Pianezzi, E., et al., ("Role of somatic cell sources in the maturation degree of human induced pluripotent stem cell-derived cardiomyocytes". Biochim Biophys Acta Mol Cell Res, 2019: p. 118538).

Differentiated cells displayed spontaneous beating activity at 10.0±1.4 day post infection. Fifteen days after the onset of spontaneous beating activity, beating iPSC-CMs were detached from culture wells by microdissection and gently plated onto a multielectrode arrays plate (MEA) with standard 60 electrodes. MEAs with high spatial (200 mm) resolution (60 MEA-200/30iR-Ti; Multi Channel Systems, Reutlingen, Germany) were used. Extracellular field potentials (FPD) were recorded on spontaneously beating clusters of iPSC-CMs at 37° C.

Salvia haenkei (SH) extract was added to the culture medium at day 1 of recording (approximately 25 days post infection, DPI) at maximum concentration of 10 µg/ml (FIG. 1A). Field-potential duration, reflecting electrical systole, was measured from the onset of the sharp positive deflection to the peak of the secondary slow deflection (FIG. 1B); for simplicity, this measurement is indicated as "QT", which was rate corrected (QTc) by Bazett's formula.

As shown in FIG. 1C, SH did not cause any statistically significant variation in QT interval; therefore, in basal condition electrophysiological properties of CMs are not affected by the presence of SH at 10 µg/ml.

Example 3

SH Effects on Electrophysiological Properties of Beating Human iPS-CM (with Cardiotoxic Treatment)

Figure 2:
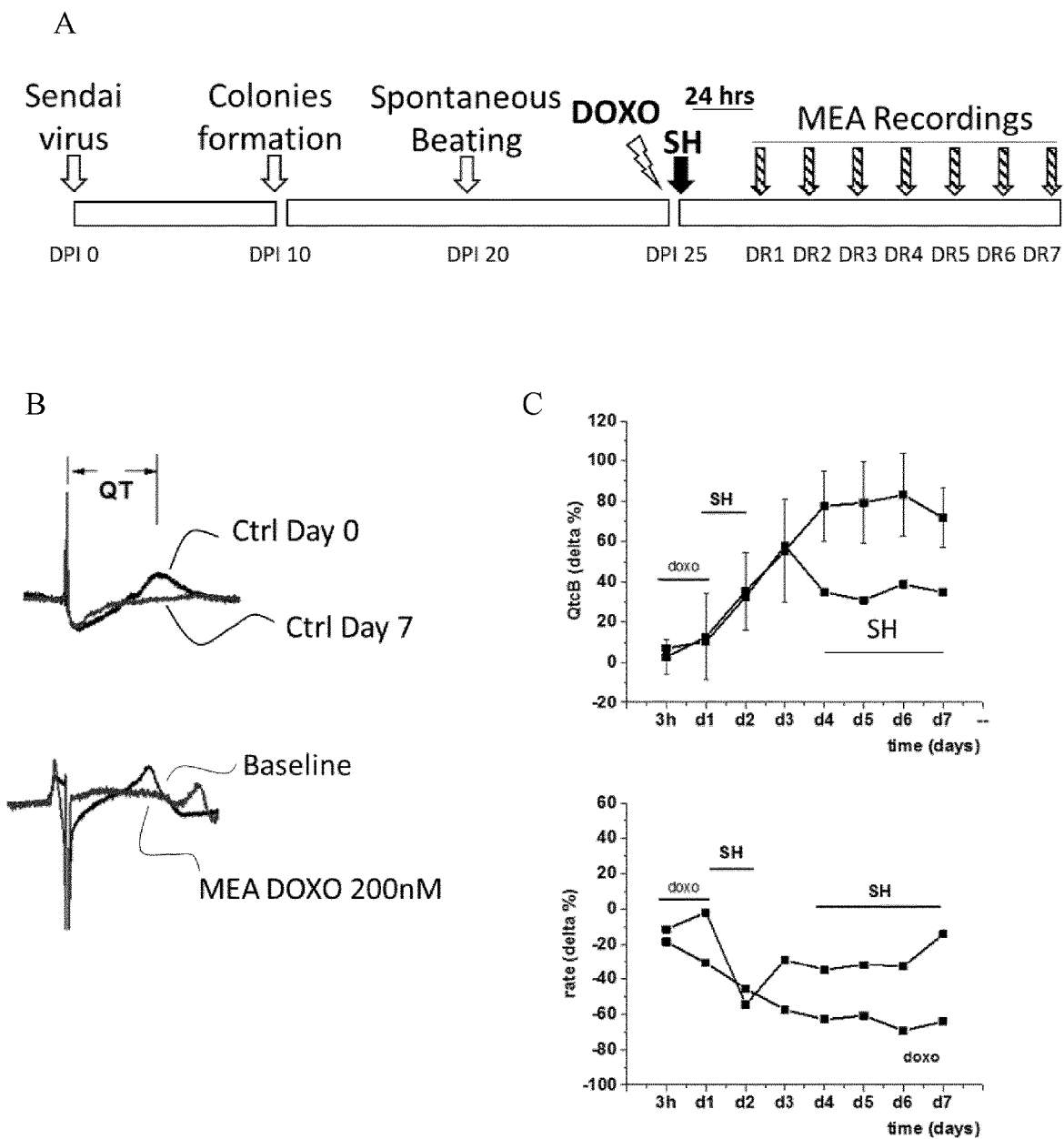
FIG. 2 shows: (A) a scheme of the protocol of the in vitro experiment of Example 3 (SH=*Salvia haenkei* extract; MEA=multielectrodes array, DOXO=doxorubicin), (B) exemplary ECG traces (QT interval is shown) and (C) the results of the QT recordings of SH treated and non-treated beating CMs, after DOXO exposure.

Doxorubicin (DOXO) cancer treatment at sub-lethal concentration (10-7 M) in cardiac muscle cells (CM) impairs functionality of ion channels in CM and causes cardiotoxicity with prolongation of QT interval, which underlies arrhythmogenic cardiomyopathy in patients. A platform for modelling DOXO-induced electrophysiological dysfunction, recently developed, has been employed here to test whether SH may rescue detrimental effect of DOXO on QT interval. DOXO was added to the medium of beating CM and after 3 hours the medium was changed and SH added at concentration of 10 µg/mL (FIG. 2A).

Traces were recorded every 24 hours for 7 consecutive days from the beginning of the DOXO treatment (day 0-3 h).

As expected, the treatment with DOXO induces prolongation on QT interval that was surprisingly reverted by treatment with SH. SH has also a positive effect in stabilizing beating rate (FIG. 2C).

Example 4

Cardioprotective Role of SH in an Animal Model of Cardiotoxicity

Adult female Sprague-Dawley rats (250-300 g body weight) were injected with six intraperitoneal doses of DOXO (Sigma) delivered at regular intervals from Day 1 to Day 11 (cumulative dose=15 mg/kg). During the treatment, rats were given ad libitum access to water containing SH. Rats received a daily dose of about 0.5 mg/Kg of SH.

Echocardiographic assessment, animals were anaesthetized at the indicated time points with 2.0-2.5% isoflurane. Transthoracic echocardiography was performed using the Vevo 2100 high-resolution imaging system (VisualSonic) equipped with a 13-24-MHz linear transducer. Analyses were performed on Days 0 (baseline), 12, 19. Two-dimensional short-axis M-mode echocardiography was performed. All M-mode tracing measurements were averaged from a minimum of three cardiac cycles. Investigators were blinded to the animals' identity.

Figure 3:
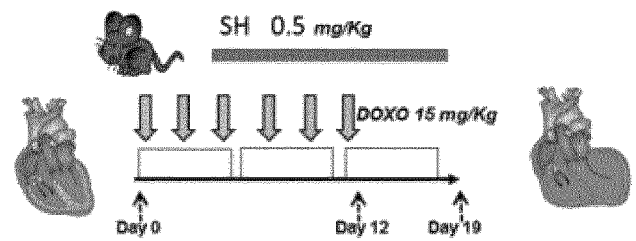
FIG. 3 shows: (A) a scheme of the protocol of the in vivo experiment of Example 4, (B) representative echocardiography images of each group tested and (C) quantification of the results.
Figure 3:
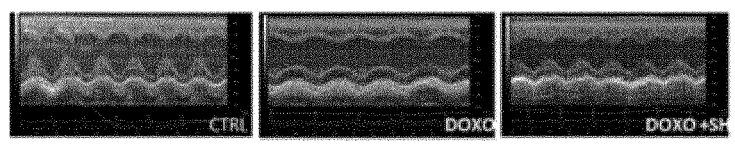
Figure 3:
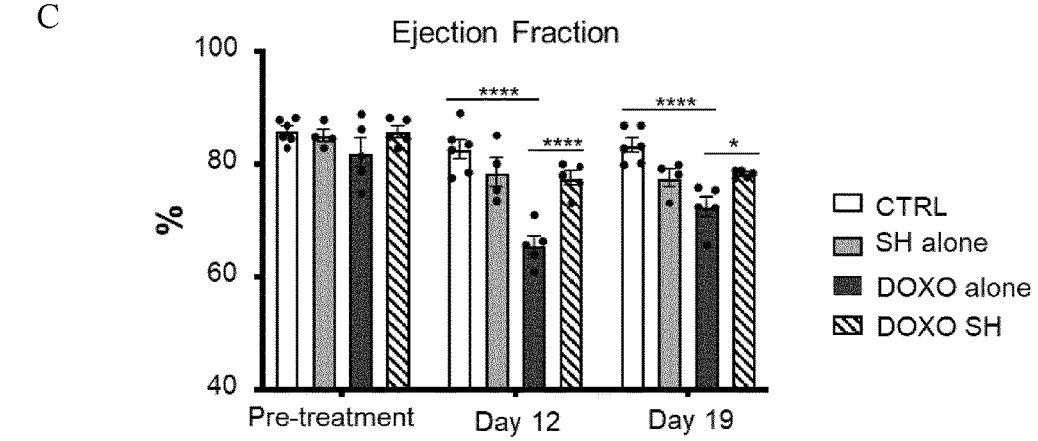
Figure 3:
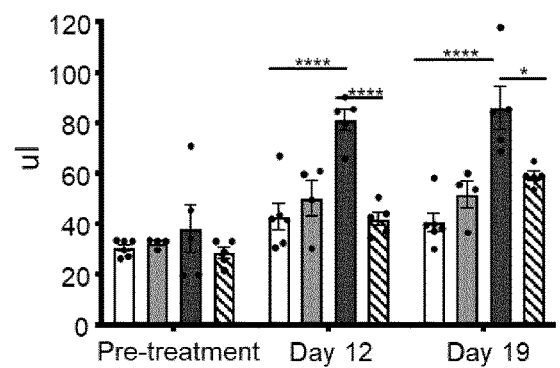
Figure 3:
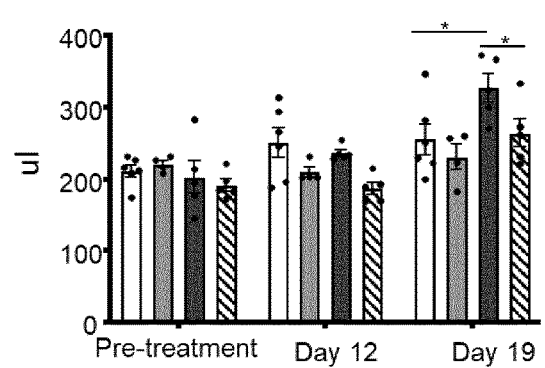

Representative echocardiography images for the three different groups of treatment at 12 days are shown in FIG. 3B. In DOXO-treated animals not receiving SH, the left end systolic volume (LVESV), increased over time, with a consequent significant decrease in left ventricular ejection fraction (LVEF). Simultaneously administration of SH significantly reduced LVESV while increasing LVEF on days 12, and 19. Left ventricular end diastolic volume (LVEDV) was also significantly reduced at day 19 (FIG. 3C). These results show that SH prevents DOXO-induced detrimental effect on heart global function.

Advantageously, SH alone has no effect on heart function in untreated and unaffected animals (FIG. 3C).

Example 5

SH Effects on Reducing Collagen-I Secretion by Fibroblast

Figure 4:
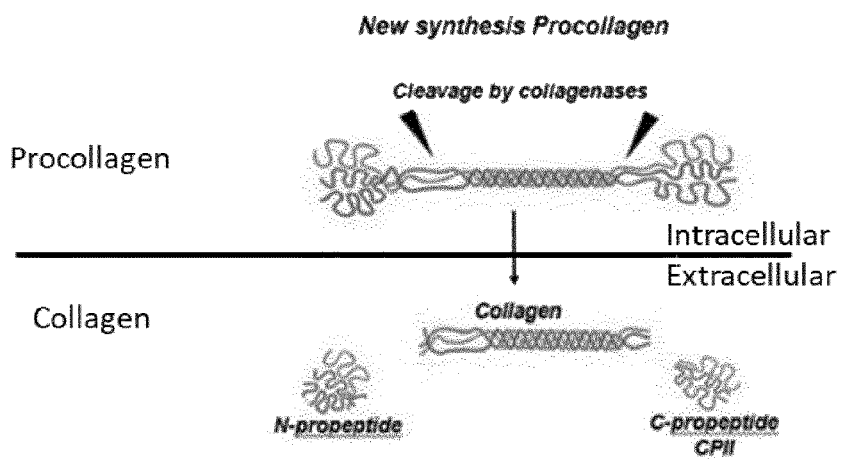
FIG. 4 shows: (A) a scheme of collagen synthesis, and the evaluation of formation of both procollagen and secreted collagen-I by cardiac fibroblast at basal level and following exposure to Tgfb-1, with or without SH, as per Example 5 (Western Blot analysis and the quantitative results are shown respectively in B and C panels).
Figure 4:
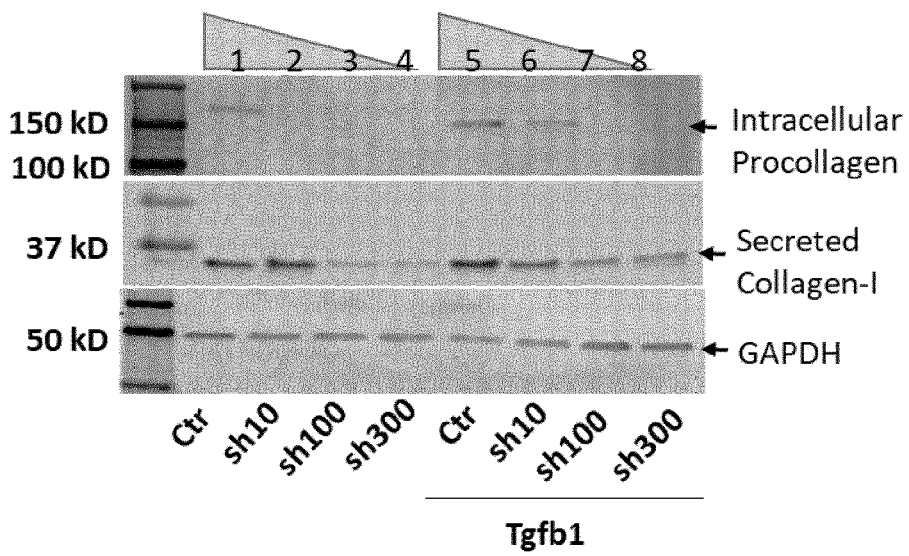
Figure 4:
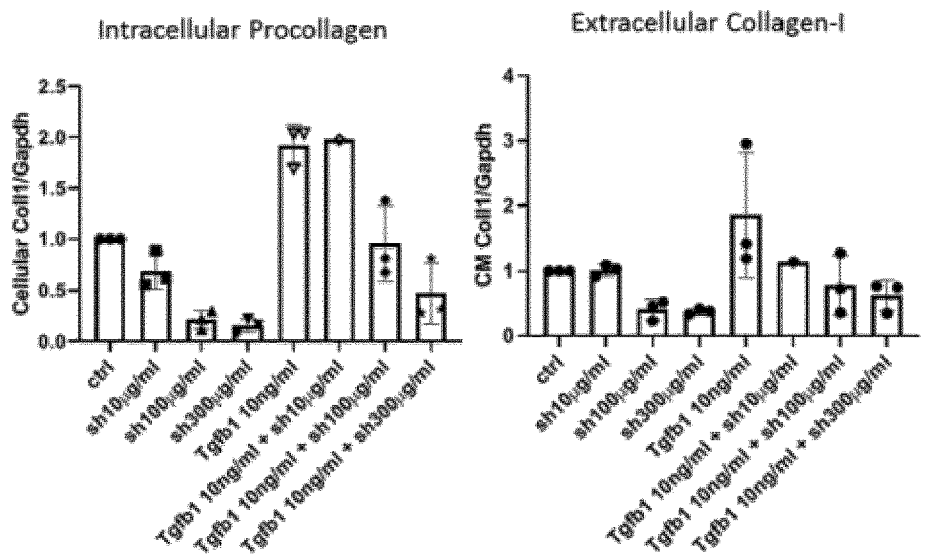

Collagen biosynthesis and secretion by cardiac activated fibroblast (myofibroblast) is a key phenomenon that regulate fibrosis in the heart, leading to maladaptive remodeling in heart failure. Collagen is synthesized as pre-pro-α-chains that after multiple steps of posttranslational modifications, self-assembles in the triple helix called procollagen. The procollagen is excreted and is converted extracellularly into collagen by cleaving the propeptides (FIG. 4A). By using an antibody direct against the C-peptide CPII, it is possible to distinguish intracellular procollagen from the extracellular isoform.

SH ability to reduce the formation of both procollagen and secreted collagen-I by cardiac fibroblast was tested at basal level and following activation in myofibroblast by exposure to Tgfb-1.

As shown by representative immunoblotting analysis (FIG. 4B, 4C) SH reduces collagen synthesis in cardiac fibroblast at basal level as well as after stimulation with Tgfb-1.

The effect is dose-dependent and outperforms for secreted collagen-I, thus showing that SH reduce deposition of collagen in fibrotic heart.

Without being bound to theory, this effect is most likely behind the cardioprotective effect observed in-vivo (see Example 4).

Figure 5:
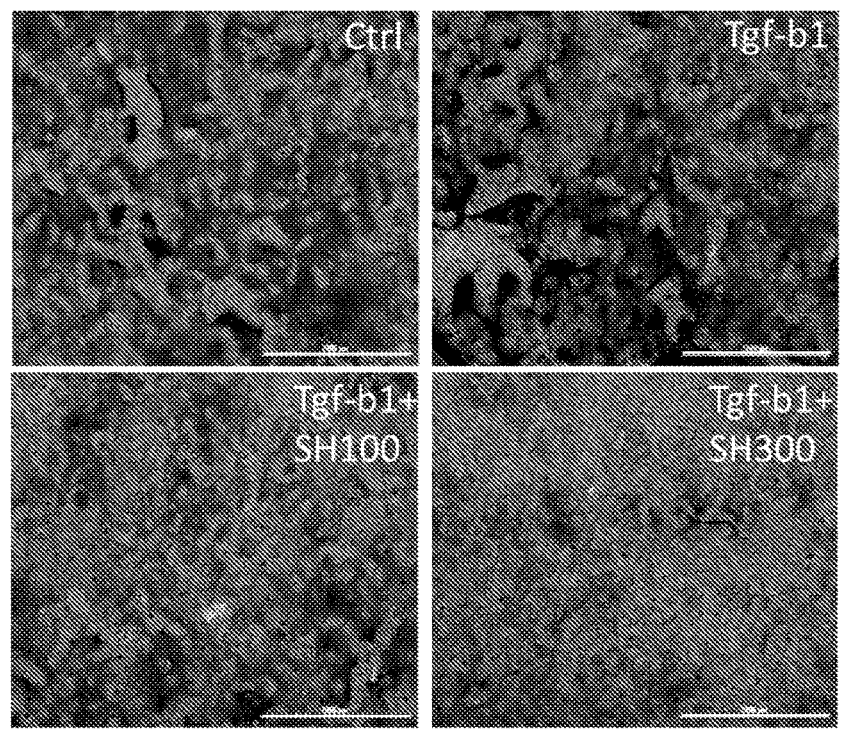
FIG. 5 shows: (A) the staining of collagen-I and collagen-II fibers in cardiac fibroblast, at basal level and following exposure to Tgfb-1, with or without SH, as per Example 5, and the quantification of said staining (B).
Figure 5:
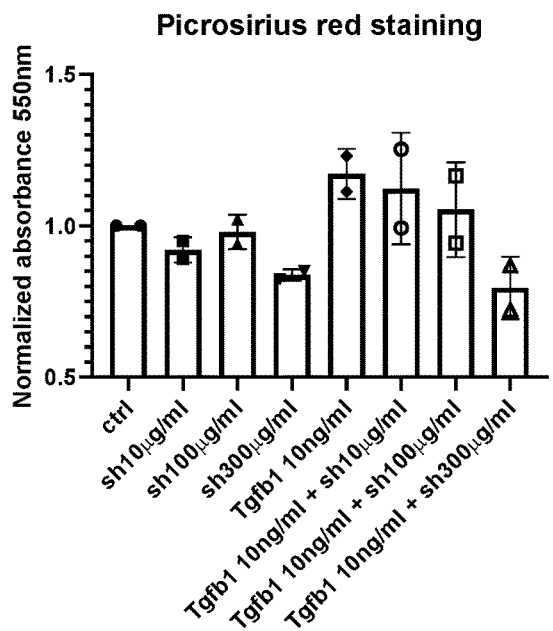

The effect of SH in reducing collagen deposition was further assessed by "picrosirious red", which stains collagen-I and collagen-II fibers (FIG. 5A).

As shown by the representative images and quantification (FIG. 5B), SH has no effects in terms of fibers deposition in basal condition, while it significantly reduces the collagen secretion and fibers formation upon fibroblast activation by Tgf-b stimulus.

The invention claimed is:

1. A method of improving, slowing, relieving and/or reducing heart disease in a subject in need thereof, said method comprising:
   administering to a subject in need thereof a Salvia haenkei extract as an active agent, wherein said heart disease is at least one of: cardiac fibrosis, arrythmia, long QT syndrome (QTL), heart failure, heart attack and cardiotoxicity, wherein said heart disease is induced by drugs.

2. The method of claim 1, wherein said heart disease is cardiac fibrosis.

3. The method of claim 1, wherein said heart disease is cardiotoxicity.

4. The method of claim 1, wherein said extract is to be administered via oral route.

5. The method of claim 1, wherein said extract is to be administered in a dose of 1-5000 mg per day.

6. The method of claim 1, wherein the *Salvia haenkei* extract is in the form of a pharmaceutical composition further comprising pharmaceutically acceptable vehicles.

7. The method of claim 6, wherein said pharmaceutical composition is in the form of tablets, capsules, lozenges, orodispersible films, soft gelatin capsules, granulates or powder, orodispersible powder, liquid solutions, dressing, suspensions, or a combination thereof.

8. The method of claim 1, wherein the *Salvia haenkei* extract is in the form of a food supplement.

9. The method of claim 6, wherein the pharmaceutical composition comprises *Salvia haenkei* extract in a concentration of 0.1-500 mg/ml when in liquid form, or of 0.1-500 mg/mg when in solid form, of the composition.

10. The method of claim 6, wherein the pharmaceutical composition comprises *Salvia haenkei* extract in a concentration of 0.1-500 mg/ml when in liquid form, or of 0.1-500 mg/mg when in solid form, of the supplement.

11. The method of claim 1, wherein the drugs are chemotherapy drugs.

* * * * *